United States Patent
Takeda

(10) Patent No.: US 7,410,257 B2
(45) Date of Patent: Aug. 12, 2008

(54) SLIT LAMP MICROSCOPE

(75) Inventor: Takanori Takeda, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 545 days.

(21) Appl. No.: 11/037,187

(22) Filed: Jan. 19, 2005

(65) Prior Publication Data

US 2005/0185136 A1  Aug. 25, 2005

(30) Foreign Application Priority Data

Feb. 10, 2004 (JP) ............................. 2004-033816

(51) Int. Cl.
*A61B 3/10* (2006.01)
(52) U.S. Cl. ...................... 351/214; 251/221
(58) Field of Classification Search ................. 351/214, 351/221, 245
See application file for complete search history.

(56) References Cited

U.S. PATENT DOCUMENTS

| | | | | |
|---|---|---|---|---|
| 4,331,392 A * | 5/1982 | Sato | ........................... | 351/214 |
| 4,818,068 A | 4/1989 | Takagi | ........................ | 350/272 |
| 5,661,589 A | 8/1997 | Meyer | ......................... | 359/232 |
| 6,072,623 A * | 6/2000 | Kitajima et al. | ............. | 359/368 |
| 6,252,696 B1 * | 6/2001 | Koschmieder et al. | ...... | 359/232 |
| 2004/0070807 A1 * | 4/2004 | Hoshino | ..................... | 359/232 |

FOREIGN PATENT DOCUMENTS

| | | |
|---|---|---|
| JP | 5-184543 | 7/1993 |
| JP | 2003-299619 | 10/2003 |

OTHER PUBLICATIONS

European Search Report of May 19, 2005.
Patent Abstracts of Japan vol. 2003, No. 12, Dec. 5, 2003 & JP 2003-299619 A (Topcon Corp), Oct. 21, 2003.
Patent Abstracts of Japan vol. 017, No. 597 (C-1127), Nov. 2, 1993 & JP 05-184543 A (Kowa Co), Jul. 27, 1993.

* cited by examiner

*Primary Examiner*—Jordan M. Schwartz
*Assistant Examiner*—James C Jones
(74) *Attorney, Agent, or Firm*—Edwards Angell Palmer & Dodge LLP

(57) ABSTRACT

Disclosed is a slit lamp microscope capable of forming a slit superior in terms of parallelism. The slit lamp microscope includes casings (100L and 100R) to the bottoms surfaces of which slit blades (107L) and (107R) are fixed and which are connected together so as to be rotatable around shaft members (102), and an inter-casing distance varying member (87) adapted to change the distance between the casings (100L and 100R) in correspondence with vertical movement of an ascent/descent shaft (86). Coil-like portions of torsion springs (103) are wound around the shaft members (102) to which the casings (100L and 100R) are connected. The torsion springs (103) urge the casings (100L and 100R) so as to bring the slit blades (107L and 107R) close to each other. Further, the casings (100L and 100R) are equipped with U-shaped springs (106) urging protrusions (100L' and 100R') thereof so as to press them against the shaft members (102).

4 Claims, 10 Drawing Sheets

(A)

103

(B)

103

106

SLIT LAMP MICROSCOPE

BACKGROUND OF THE INVENTION

1. Field of the Invention

The present invention relates to a slit lamp microscope for use in a field of ophthalmology, and more specifically to a slit lamp microscope with a special contrivance in its portion related to the formation of a slit.

2. Description of the Related Art

A slit lamp microscope has been used as a kind of microscope for use in the field of ophthalmology. A slit lamp microscope, which makes it possible to observe various lesion parts of an eye to be examined through a contrivance in illumination, is used for day-to-day diagnosis by eye doctors.

JP2003-299619 A (claims, paragraphs [0019] to [0026] in the specification, and FIGS. 1 and 2) discloses an example of the construction of a conventional slit lamp microscope. The slit lamp microscope as disclosed in the above-mentioned publication includes: an illumination system which applies slit light to the eye to be examined (hereinafter simply referred to as "the eye") through a prism to make it possible to observe a sectional image of the portion of the eye to be observed; a background illumination system which illuminates the periphery of an illumination field of the eye given by the illumination system to make it possible to observe the portion of the eye to be observed and the periphery thereof; an observation system for observing the portion of the eye to be observed and the periphery thereof; a stationary guide member detachably arranged in the vicinity of the prism of the illumination system; and an irradiation unit which holds a light guide member guiding background illumination light from a light source provided in the illumination system, which is arranged so as to draw a turn track with respect to the stationary guide member around the reflection point of the prism or a point in the vicinity thereof, and which applies background illumination light emitted from the light guide member to the prism from a different direction to change the irradiation field with respect to the eye, whereby it is possible to clearly observe not only the lesion part of the eye but, at the same time, the entire image thereof.

In the following, the construction of the conventional slit lamp microscope as disclosed in JP 2003-299619 A will be described with reference to FIGS. 8 through 11. FIG. 8 is a schematic side view showing the external construction of the slit lamp microscope. FIG. 9 is a schematic side view showing the optical configuration of the slit lamp microscope. FIGS. 10 and 11 are a perspective view and a plan view schematically showing how a slit is formed in the slit lamp microscope.

As shown in FIG. 8, the slit lamp microscope 1 includes a base 4 supported on a table 2 so as to be capable of being moved in a lateral horizontal direction and a longitudinal horizontal direction by means of a movement mechanism portion 3, an operating handle (joy stick) 5 adapted to displace the base 4 in the lateral horizontal direction and the longitudinal horizontal direction through tilting operation, an observation system 6 and an illumination system 8 supported by the base 4, and a-chin-rest stand 10 equipped with a chin rest 10a and a forehead pad 10b for the subject arranged opposite to a lens barrel main body 9 accommodating the observation system 6. Provided on a side surface of the lens barrel main body 9 is an observation power adjusting knob 11 for varying the observation power. Further, an imaging device 20, such as a CCD, is connected to the lens barrel main body 9. Further, below the observation system 6, there is arranged a prism 12 for reflecting observation light in the direction of the eye (not shown).

As shown in FIG. 9, the observation system 6 of the slit lamp microscope 1 includes the prism 12, an objective lens 31, a scaling optical system 32, a condensing lens 33, a beam splitter 34, a relay lens 35, a prism 36 for shifting the optical path to the eyepiece lens barrel 9a side, and an eyepiece 37 arranged in the eyepiece lens barrel 9a. An image of the eye E of the subject is formed at an image formation point P, and is observed by an eye Eo of the examiner.

The imaging device 20 includes a condensing lens 41 for condensing the light branched off by the beam splitter 34, a mirror 42 reflecting the light from the condensing lens 41 at right angles, and an imaging camera 43 consisting of a CCD or the like.

The illumination optical system 21 constituting the illumination system 8 includes a light source 51 consisting of a halogen lamp or the like, condensing lenses 52 and 53 for condensing light emitted from the light source 51, a slit 54 allowing transmission of only a portion of the light transmitted through the condensing lenses 52 and 53 to form slit light, a condensing lens 55 condensing the light transmitted through the slit 54, and a strobe light source 56 consisting of a xenon lamp or the like arranged between the light source 51 and the condensing lens 52.

The slit 54 and the eye E are arranged at positions optically conjugate with respect to the condensing lens 55. As a result, slit light (local illumination light) is applied, for example, to the cornea of the eye E, making it possible to observe a sectional image of the cornea.

A background illumination system 70 includes a light guide 71 consisting of an optical fiber serving as a light guide member led out from a position in the vicinity of the light source 51, and an irradiation unit 74 which holds the light guide 71 and which is provided so as to draw a turn track around a reflection point R of the guided light at the prism 12. Part of the light from the light source 51 is guided to the irradiation unit 74 by the light guide 71. The irradiation unit 74 projects the guided light onto the prism 12 from a direction different from that of the light from the illumination system 8 to irradiate the eye E with the light. As a result, the periphery of the lesion part of the eye E is irradiated with the light. The irradiation unit 74 is capable of changing the irradiation field with respect to the eye E.

The slit 54 of the illumination system 8 is formed by a slit forming means 100' as shown in FIG. 10. The slit forming means 100' includes left and right casings 100L and 100R. FIG. 11 is a top view of the casings 100L and 100R. When it is said right or left, it means here the direction as seen from the examiner, that is, the direction as seen from the eyepiece lens barrel 9a shown in FIG. 8.

The casings 100L and 100R are arranged so as to form a cylinder with a gap 109 therebetween. Further, the casings 100L and 100R respectively have pairs of protrusions 100L' and 100R' arranged at positions opposed to each other. The protrusions 100L' and 100R' are configured so as to constitute a part of the cylinder. Further, as shown in FIG. 11, formed in the bottom surfaces of the casings 100L and 100R are screw holes 108L and 108R for providing through threaded engagement a pair of slit blades forming the slit 54 (see slit blades 107L and 107R in FIG. 3 described below).

Protruding from the outer peripheral surfaces of the casings 100L and 100R of the slit forming means 100' are bearings 101L and 101 R so as to be spaced apart from each other by a predetermined distance. The bearings 101L and 101R are provided only on the front side as seen in FIG. 10. The protrusions 100L' of the casing 100L and the protrusions 100R' of the casing 100R are fitted into ring members 105 while holding columnar shaft members 102 therebetween. As a result, the casings 100L and 100R are connected so as to be rotatable around the shaft members 102. The shaft members 102 and the ring members 105 are provided respectively for the pairs of protrusions 100L' and 100R' arranged in an opposed relation.

When the examiner performs a predetermined operation to change the width of the slit 54, an ascent/descent shaft 86 is moved in the axial direction thereof, that is, vertically. A Mount-Fuji-shaped inter-casing distance varying member 87 with tapered sides is fixed to the upper end of the ascent/descent shaft 86 by screws 87a. The tapered sides of the inter-casing distance varying member 87 are arranged so as to be held in contact with the bearings 101L and 101R.

In order to reliably hold the side surfaces of the inter-casing distance varying member 87 in contact with the bearings 101L and 101R and to avoid slippage or the like as much as possible, the casings 100L and 100R are equipped with an urging means (not shown) consisting of a spring or the like urging the casings 100L and 100R so as to bring the above-mentioned pair of slit blades close to each other. The urging means also exerts urging force so as to press the protrusions 100L' and 100R' of the casings 100L and 100R against the shaft members 102. As the urging means, there is provided, for example, a U-shaped spring on the inner peripheral surfaces of the casings 100L and 100R. The U-shaped spring is arranged at a position lower than the shaft members 102 constituting the rotation shafts of the casings 100L and 100R, that is, at a position nearer to the slit blades than the shaft members 102.

The inter-casing distance varying member 87 moves vertically with the ascent/descent shaft 86. When it moves upwards, the inter-casing distance varying member 87 functions so as to increase the distance between the bearings 101L and 101R. As a result, the casings 100L and 100R are rotated around the shaft members 102 so as to enlarge the gap 109. With this rotation, the distance between the pair of slit blades mounted to the bottom surfaces of the casings 100L and 100R increases, and the width of the slit 54 increases. When, in contrast, the inter-casing distance varying member 87 moves downwards, the distance between the bearings 101L and 101R is reduced, and the casings 100L and 100R are rotated around the shaft members 102 so as to diminish the gap 109, reducing the distance between the pair of slit blades to diminish the width of the slit 54.

It should be noted that the slope of the sides of the inter-casing distance varying member 87 is formed so as to be relatively steep in the upper portions and relatively gentle in the lower portions thereof. Thus, when the width of the slit 54 is small, fine width adjustment is possible, and, when the width of the slit 54 is to be increased, it can be done so at a stretch.

The conventional slit lamp microscope, constructed as described above, is known to have a number of problems.

First, since the slope of the lower portions of the side surfaces of the inter-casing distance varying member 87 is gentle, slippage is likely to occur between the side surfaces and the bearings 101L and 101R, and, due to the urging force of the urging means, it can happen that slippage actually occurs to cause the slit 54 to close spontaneously. This leads to a deterioration in the accuracy in the slit width, which is of importance in observation by using the slit lamp microscope. Further, when such spontaneous closing occurs, additional time is required to re-adjust the slit width, resulting in an increase in inspection time, which leads to an increase in the physical burden on both the examiner and subject. In particular, for the examiner, who has to examine a number of patients a day, such spontaneous closing of the slit is nothing but a bother.

When the urging force is weakened in order to avoid slippage between the side surfaces of the inter-casing distance varying member 87 and the bearings 101L and 101R, the connection between the casings 100L and 100R and the shaft members 102 is loosened, so that there is a fear of a problem arising in terms of the parallelism of the slit as described below.

To prevent spontaneous closing of the slit, there is often provided a brake means for braking the descent of the ascent/descent shaft 86 and the inter-casing distance varying member 87. Usually, this brake means is accommodated in a knob for performing the operation of opening or closing the slit, and consists of something like a disk brake for restraining rotation of the knob. In a typical case, a felt member is used as the disc, and braking is effected by compressing the felt member by means of a spring or the like through the inter-mediation of a washer or the like. Apart from this, a brake means is used which restrains knob rotation through adoption of a wave washer.

In such conventional brake means, which is adapted to restrain knob rotation as described above, the rotation of the knob is rather heavy. Accordingly, a great force is needed when adjusting the slit, which is disadvantageous in terms of operability.

It might be possible to effect design change so as to make the slope of the side surfaces of the inter-casing distance varying member 87 steeper; it should be noted, however, that the conventional slope configuration has been adopted for such a long time that many examiners are quite used to the relationship between its operating amount and slit width change; thus, such design change is not so desirable from the viewpoint of operability.

Another problem in the prior art is related to the parallelism of the slit. When observing and inspecting an eye by using a slit lamp microscope, it is desirable for the slit to be formed parallel. In the prior-art technique, however, there are cases in which it is rather difficult to form the slit parallel. It is to be assumed that the difficulty is due partly to the heat of the light source and partly to the accuracy at the time of production.

When a slit lamp microscope is used for a long period of time, the interior of the apparatus may attain high temperature due to the heat from the light source. The temperature attained can be as high as approximately 60° C. In view of this, the ring members 105 are formed in a somewhat large size taking into account the thermal expansion of the protrusions 100L' and 100R' of the casings 100L and 100R, of the shaft members 102, and, further, of themselves. Accordingly, depending upon the temperature inside the apparatus, the connection between the protrusions 100L' and 100R', the shaft members 102, and the ring members 105 can be loosened. That will make it impossible for the casings 100L and 100R to rotate uniformly to the right and left, resulting in formation of a distorted slit which is not parallel.

Similarly, the parallelism of the slit can be influenced by production errors in the casings 100L and 100R, the shaft members 102, and the ring members 105.

SUMMARY OF THE INVENTION

The present invention has been made in view of the above problems in the prior art. It is an object of the present invention to provide a slit lamp microscope allowing formation of a slit superior in terms of parallelism.

Another object of the present invention is to provide a slit lamp microscope allowing the slit width changing operation to be performed easily and capable of preventing spontaneous closing of the slit.

To attain the above objects, according to a first aspect of the present invention, there is provided a slit lamp microscope characterized by including: an illumination system which has a light source emitting illumination light and a pair of slit forming members spaced apart from each other to allow passage of a part of the illumination light and which is adapted to apply slit light to an eye to be examined; a slit width changing means having a pair of holding members respectively holding the pair of slit forming members, a shaft member supporting the pair of holding members such that the pair of holding members can rotate in opposite directions, and an engagement portion arranged between the pair of holding members and engaged with each of the pair of holding members, the engagement portion being capable of vertical displacement, the vertical displacement being converted to displacement in the opposite directions of the pair of holding members around the shaft member, the slit width changing means being adapted to change an opening width of the slit in correspondence with the displacement in the opposite directions of the pair of holding members; an observation system receiving reflection light of the slit light applied to the eye to be examined; a first urging means for urging the pair of holding means such that bring the pair of slit forming members are brought close to each other; and a second urging means for urging the pair of holding members such that the pair of holding members are pressed against the shaft member.

Further, to attain the above objects, according to a second aspect of the present invention, the slit lamp microscope according to the first aspect is characterized in that the urging force of the second urging means is arranged to be weaker than the that of the first urging means.

Further, to attain the above objects, according to a third aspect of the present invention, the second urging means is a spring member.

Further, to attain the above objects, according to a fourth aspect of the present invention, the slit lamp microscope according to the third aspect is characterized in that the spring member is a U-shaped spring whose ends are respectively fixed to the pair of holding members.

Further, to attain the above objects, according to a fifth aspect of the present invention, the slit lamp microscope according to the fourth aspect is characterized in that: the pair of slit forming members are held at bottom surfaces of the pair of holding members: the shaft member supports the pair of holding members at a position above the pair of slit forming members; and the ends of the U-shaped spring are each fixed to the pair of holding members at one of a position above an axial center of the shaft member or a position beside the axial center.

According to the present invention, there is provided the second urging means for urging the pair of holding members so as to press them against the shaft member, so that the holding members can rotate around the shaft member in a stable manner. This helps to achieve an improvement in the parallelism of the slit formed by the gap of the slit forming members held by the holding members, making it possible to generate high precision slit light.

Further, according to the present invention, there can be made the position of the urging means for urging the pair of holding members so as to cause the pair of slit forming members to move away from each other with an urging force weaker than that of the first urging means that urges the pair of slit forming members so as to bring them close to each other, the second urging means acts so as to cancel a part of the urging force of the first urging means. Thus, when rotating the pair of holding means to change the slit width, the requisite force for the operation of vertically moving the first engagement member of the engagement portion of the slit width changing means can be small, so that the examiner can change the slit width easily.

Furthermore, due to the canceling of a part of the urging force of the first urging means by the second urging means, the force applied to the pair of holding members becomes more stable, whereby it is possible to prevent spontaneous closing of the slit.

DETAILED DESCRIPTION OF THE PREFERRED EMBODIMENT

A slit lamp microscope according to an embodiment of the present invention will be described in detail with reference to the drawings.

Figure 8:
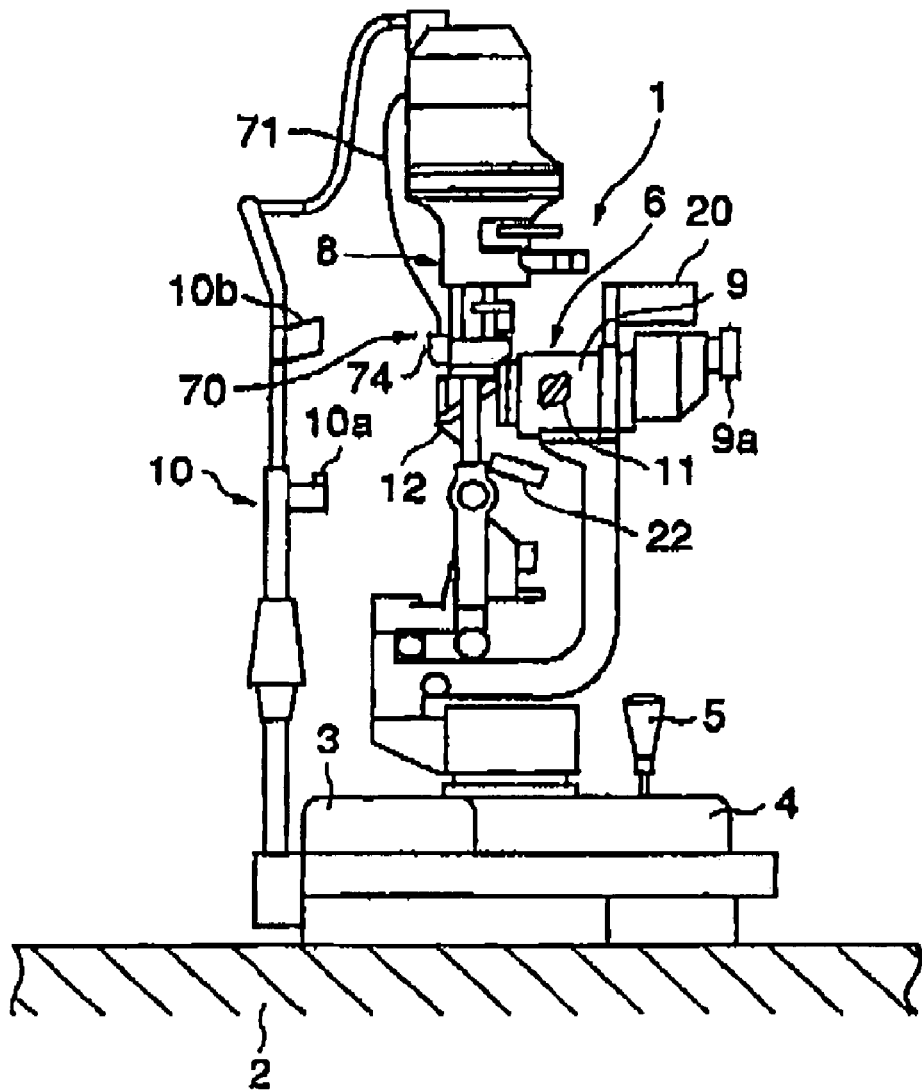
FIG. 8 is a schematic side view showing an example of an external construction of a conventional slit lamp microscope.
Figure 9:
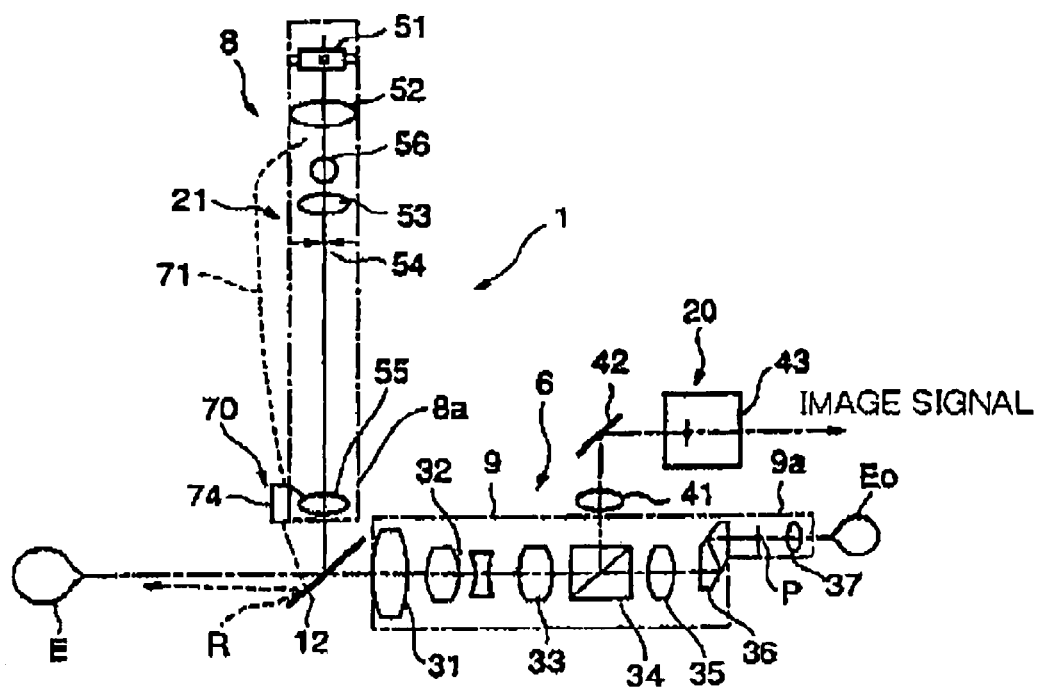
FIG. 9 is a schematic side view showing an example of an optical configuration of the conventional slit lamp microscope.
Figure 10:
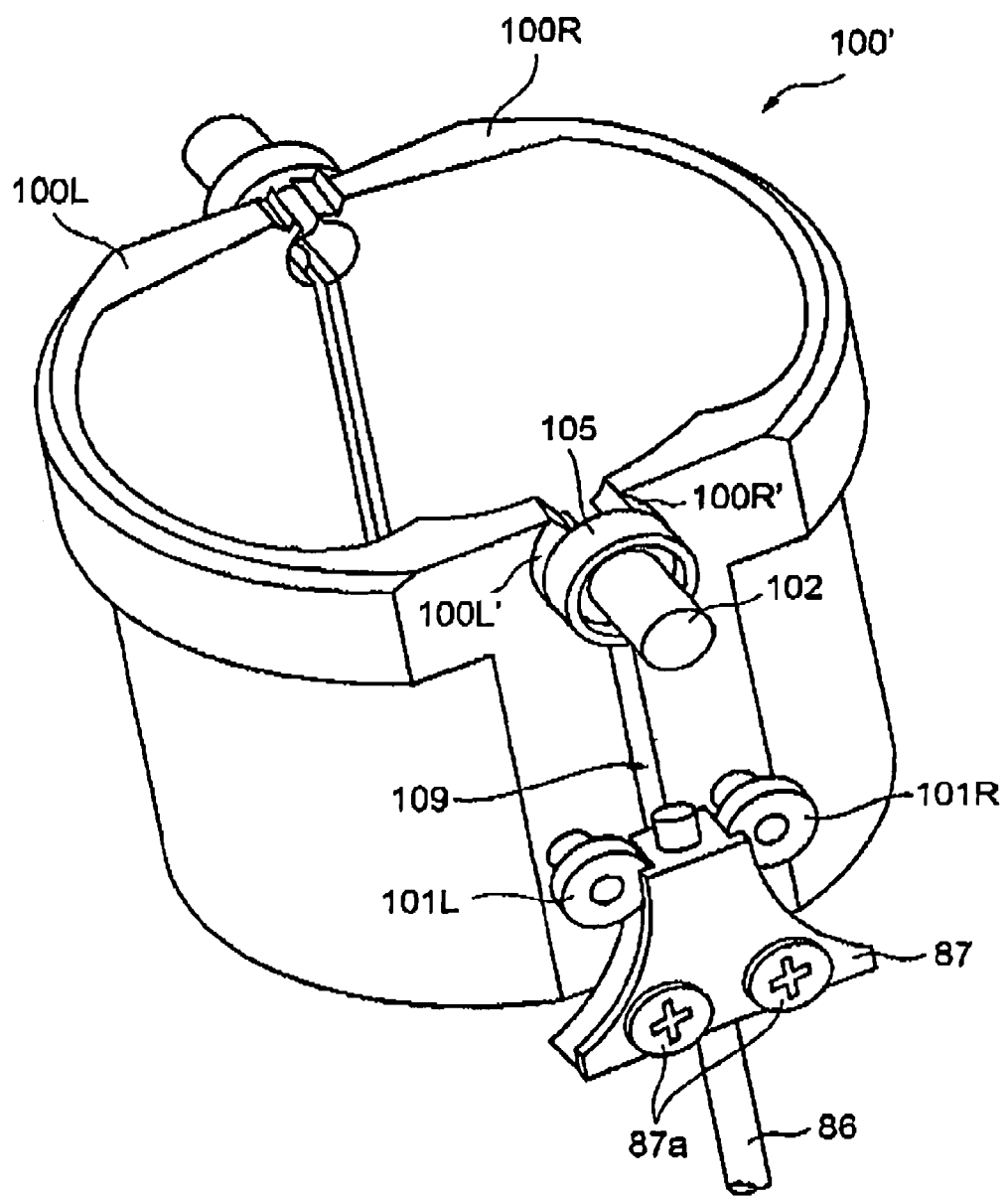
FIG. 10 is a schematic perspective view showing an example of a construction of the slit forming means of the conventional slit lamp microscope.

The slit lamp microscope of this embodiment has an external construction and an optical configuration (in particular, an observation system 6 and an illumination system 8) similar to those of the above-described conventional slit lamp microscope (see FIGS. 8 and 9). Further, this slit lamp microscope has a slit forming means substantially the same as that in the prior art (see FIGS. 10 and 11). In the following, the components that are the same as those of the conventional slit lamp microscope are indicated by the same reference numerals.

Here, the term slit forming means refers to a structure including a pair of slit blades constituting the pair of slit forming members as used in the present invention and a slit width changing means changing the slit width by changing the distance between the pair of slit blades. The term slit width refers to the width of the slit as measured in the opening direction, i.e., the opening width.

[External Construction]

Figure 1:
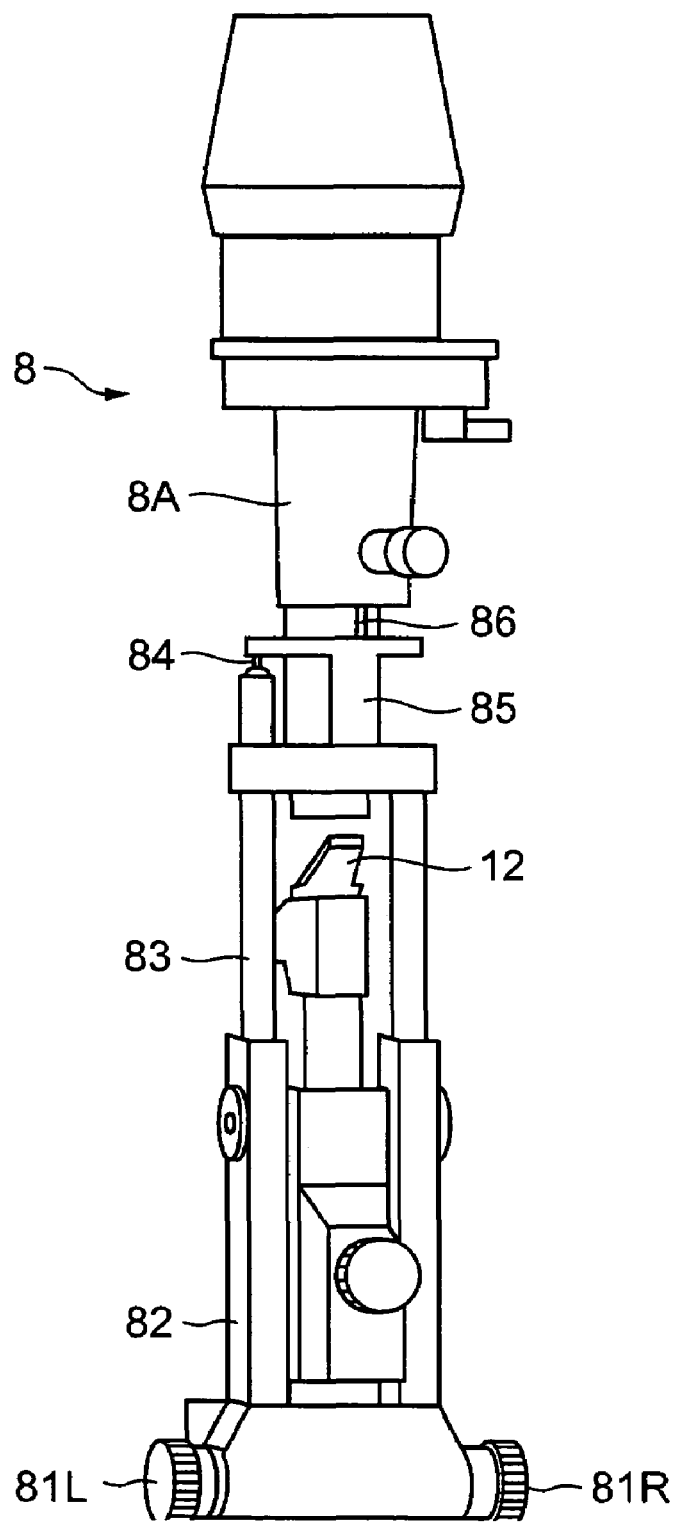
FIG. 1 is a schematic partial perspective view showing an example of an external construction of a slit lamp microscope according to an embodiment of the present invention.

FIG. 1 partially shows the external construction of the slit lamp microscope of this embodiment, more specifically, the external construction of the slit forming means thereof. The illumination system 8 shown in FIG. 9 is accommodated in a casing 8A. Illumination light (slit light) generated by the illumination system 8 is emitted from the lower end of the casing 8A, and is applied to the eye to be examined (not shown) by being reflected by a prism 12. The casing 8A is formed so as to be horizontally rotatable so as to vary the irradiating direction of the slit light with respect to the eye.

The slit lamp microscope of this embodiment is equipped with operating knobs 81L and 81R for an examiner to vary the slit width. The operating knobs 81L and 81R are formed so as to be integrally rotatable. Above the operating knob 81L, there is provided a first post 82, and a second post 83 passed through the first post 82. Inside the second post 83, there is arranged an ascent/descent shaft 84 adapted to ascend and descend as the operating knobs 81L and 81R are turned.

The upper end of the ascent/descent shaft 84 is in contact with the bottom surface of an ascent/descent table 85. The ascent/descent table 85 is adapted to move vertically as the ascent/descent shaft 84 ascends or descends. The upper surface of the ascent/descent table 85 constitutes a table spreading in the rotating direction of the casing 8A. The lower end of an ascent/descent shaft 86 capable of moving vertically abuts the upper surface of the ascent/descent table 85. The ascent/descent shaft 86 is moved as the casing 8A rotates. In this process, the lower end of the ascent/descent shaft 86 slides on the upper surface of the ascent/descent table 85. As described in detail below, the width of a slit 54 of the illumination system 8 is enlarged or diminished in correspondence with the vertical movement of the ascent/descent shaft 86.

[Internal Construction]

Referring to FIGS. 2 through 7, a slit forming means 100 for forming the slit 54 of the illumination system 8 will be described in detail. The slit forming means 100 includes a pair of slit blades 107L and 107R forming the slit 54, and a slit width changing means as described below for changing the distance between the slit blades 107L and 107R.

(Construction of the Slit Width Changing Means)

The slit width changing means of the present invention includes, in addition to the operating knobs 81L and 81R, the ascent/descent shaft 84, the ascent/descent table 85, and the ascent/descent shaft 86, which are shown in FIG. 1, a pair of left and right casings 100L and 100R, various members provided on the casings 100L and 100R, and an inter-casing distance changing member 87 which is fixed onto the upper end of the ascent/descent shaft 86 and adapted to change the distance between the casings 100L and 100R in correspondence with the vertical movement of the ascent/descent shaft 86. As described above, the inter-casing distance changing member 87 has a Mount-Fuji-like configuration having tapered side surfaces.

Figure 11:
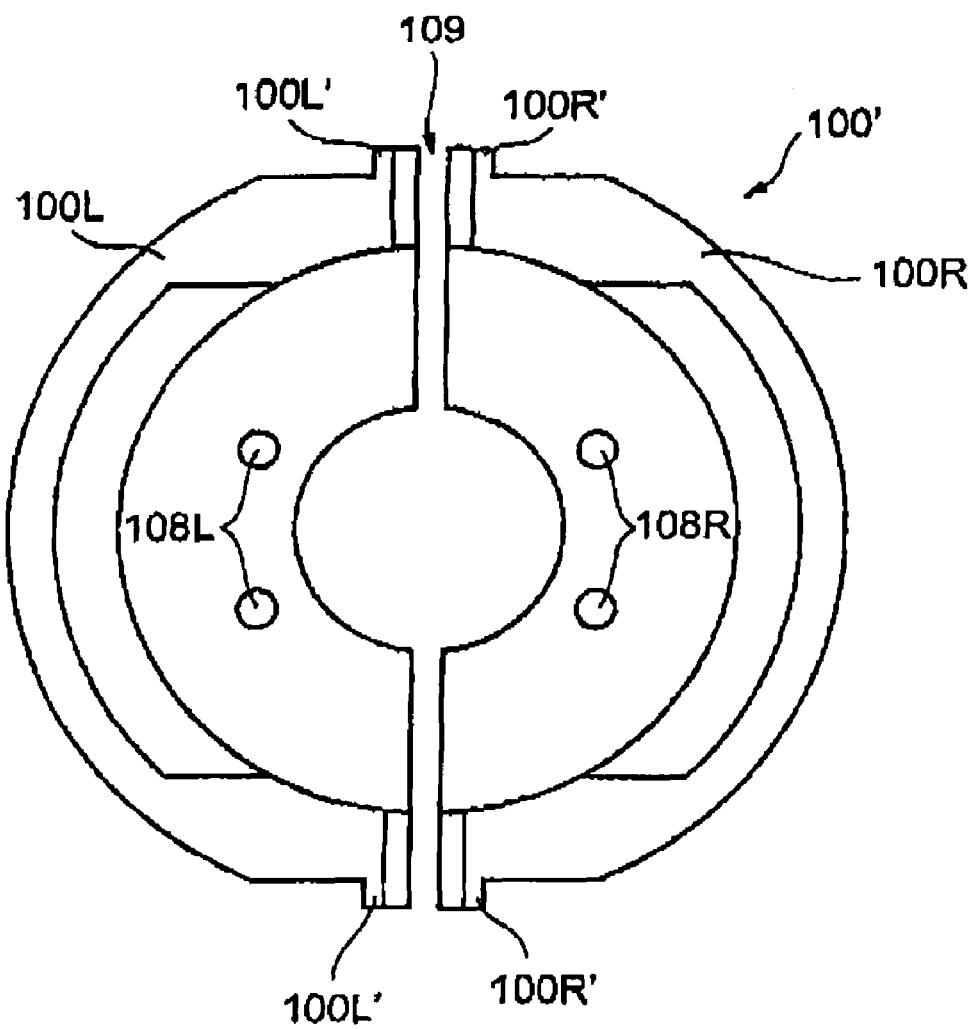
FIG. 11 is a schematic top view showing an example of the construction of the slit forming means of the conventional slit lamp microscope.

In the bottom surfaces of the casings 100L and 100R, there are formed the screw holes 108L and 108R shown in FIG. 11, and the slit blades 107L and 107R are threadedly engaged therewith.

Figure 3:
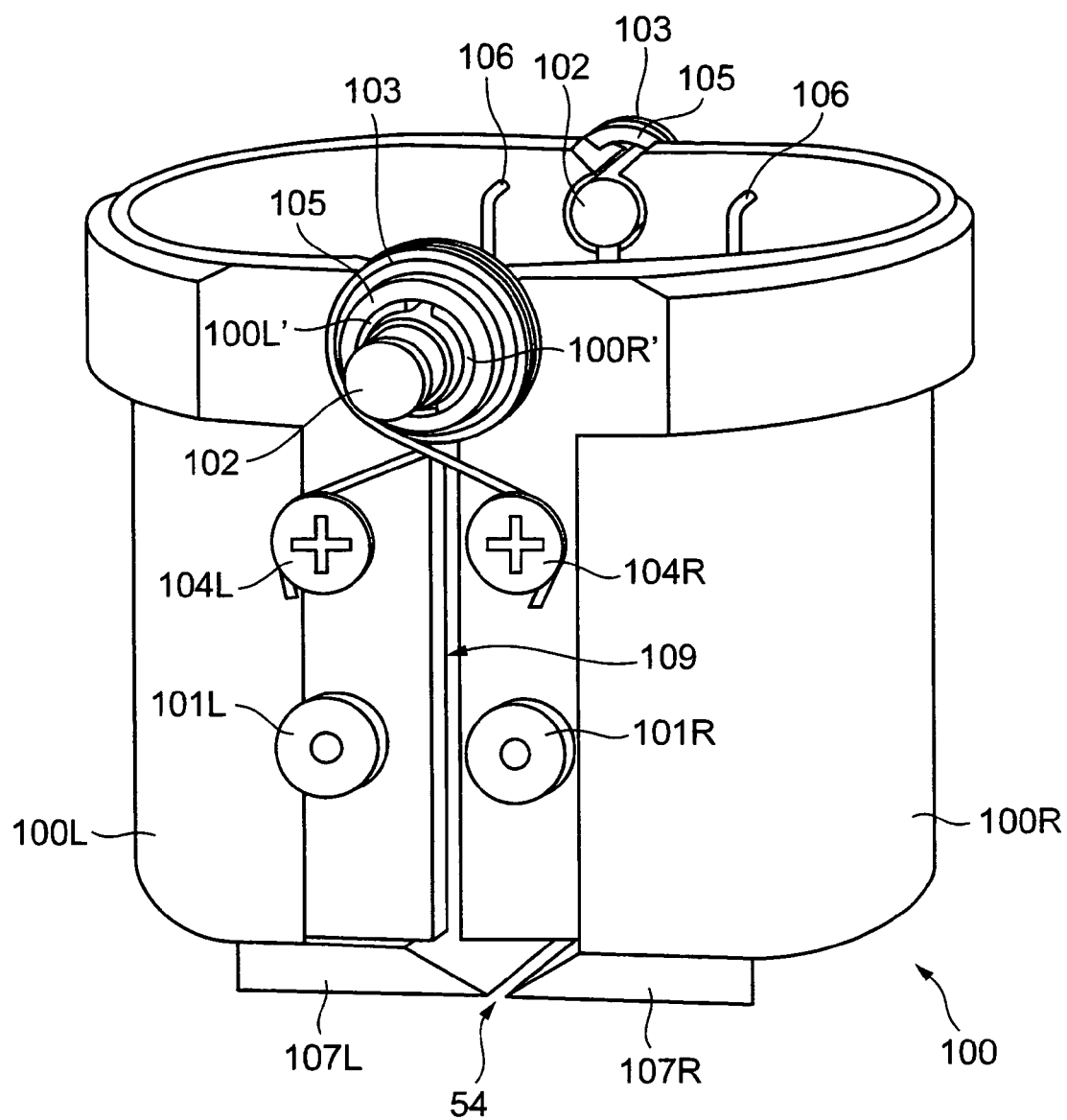
FIG. 3 is a schematic perspective view showing an example of the construction of the slit forming means of the slit lamp microscope according to the embodiment of the present invention.
Figure 4:
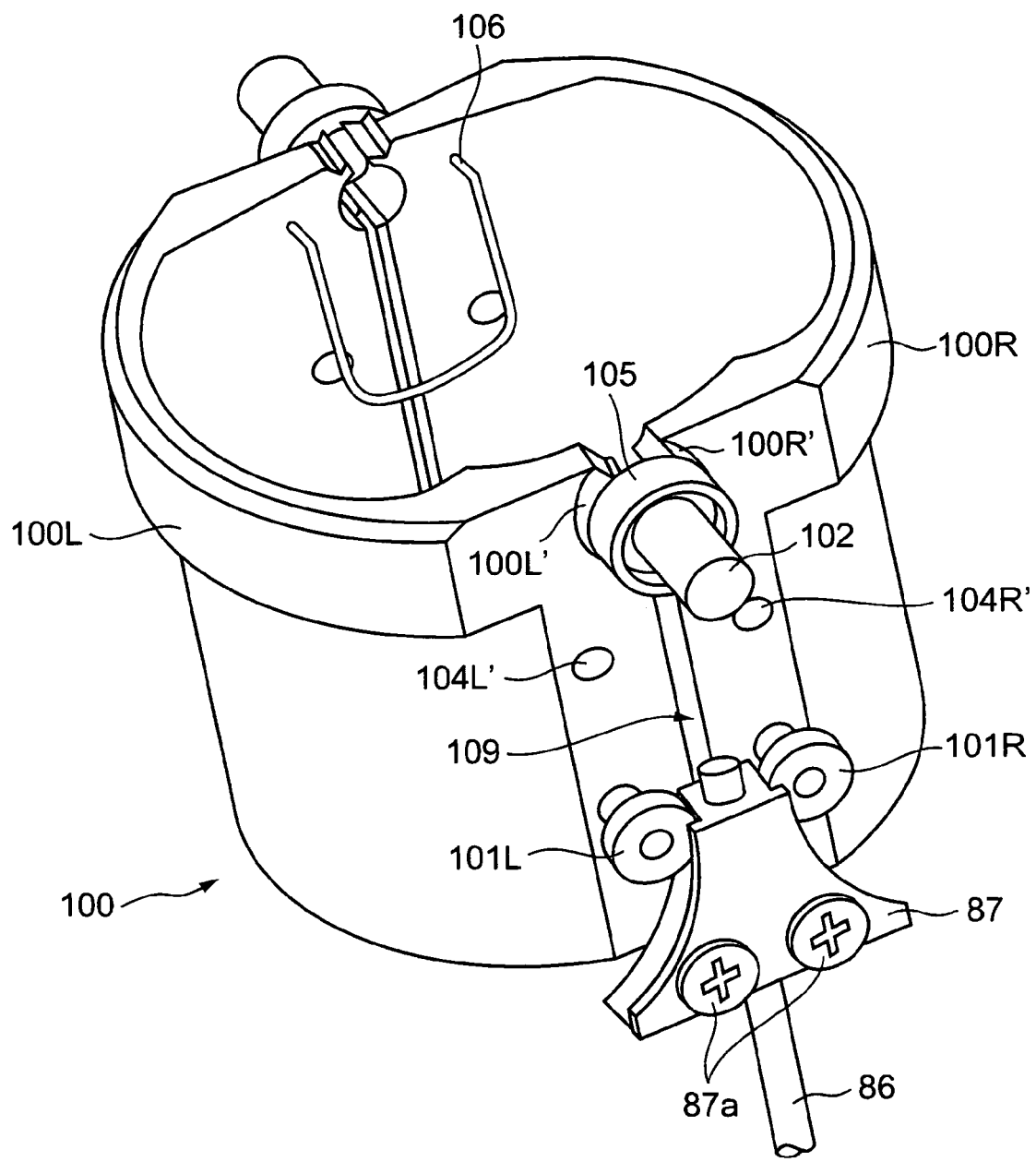
FIG. 4 is a schematic perspective view showing an example of the construction of the slit forming means of the slit lamp microscope according to the embodiment of the present invention.
Figure 5:
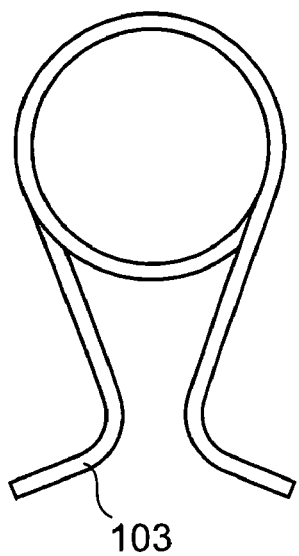
FIGS. 5A and 5B are schematic perspective views showing examples of a member constituting the slit forming means of the slit lamp microscope according to the embodiment of the present invention.
Figure 5:
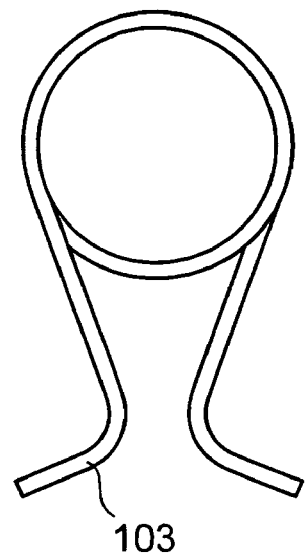

As shown in FIGS. 3 and 4, the casings 100L and 100R are arranged so as to form a cylinder with the gap 109 interposed therebetween. As shown in FIGS. 3 and 4, each of the casings 100L and 100R respectively has pairs of protrusions 100L' and 100R', which are formed at positions opposed to each other. The protrusions 100L' and 100R' are respectively configured so as to constitute a part of the cylinder, and are fitted into ring members 105 while holding columnar shaft members 102 therebetween. As result, the casings 100L and 100R are connected together so as to be rotatable around the shaft members 102. It should be noted that the shaft members 102 and the ring members 105 are respectively provided for the pairs of protrusions 100L' and 100R' arranged so as to be opposed to each other (see FIG. 3).

The casings 100L and 100R constitute a pair of holding members as used in the present invention which hold the slit blades 107L and 107R. The shaft members 102 constitutes the shaft members as used in the present invention which support the casings 100L and 100R so as to allow them to rotate in opposite directions.

Figure 2:
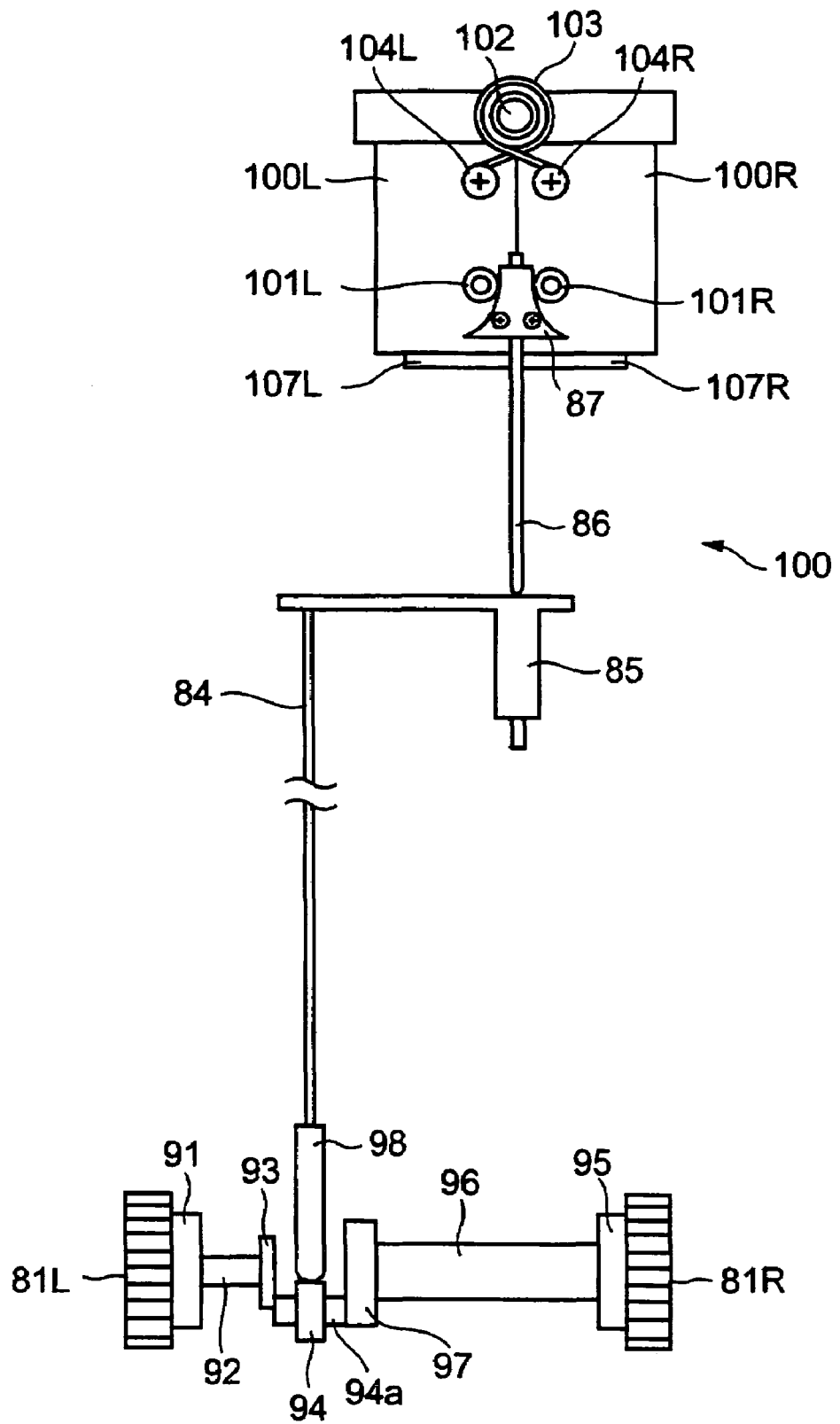
FIG. 2 is a schematic side view showing an example of a construction of a slit forming means of the slit lamp microscope according to the embodiment of the present invention.

Further, as shown in FIGS. 2 and 3, coil-like portions formed in the middle portions of torsion springs 103 are wound around the shaft members 102, the protrusions 100L' and 100R' of the casings 100L and 100R, and the ring members 105. In FIG. 4, the torsion springs 103 are omitted. The coil-like portions of the torsion springs 103 are arranged at some distance with respect to the ring members 105. One end of each coil spring 103 is fixed to the outer periphery of the casing 100L by means of a screw 104L, and the other end thereof is fixed to the outer periphery of the casing 100R by means of a screw 104R.

The torsion springs 103 urges the casings 100L and 100R so as to bring the slit blades 107L and 107R close to each other, and constitute a first urging means as used in the present invention. The reason for using the torsion springs 103 as the first urging means is that application of urging force from substantially the same direction as the rotating direction of the casings 100L and 100R makes it possible to effectively urge the casings 100L and 100R.

As shown in FIG. 3, the torsion springs 103 as described above are respectively provided around the ring members 105 arranged on the front and depth sides of the drawing so as to be opposed to each other. In this regard, the winding directions of the torsion springs 103 on the front and depth sides are opposite to each other. That is, for example, the torsion spring attached to the front side, shown in FIG. 5A, is one wound counterclockwise, and the torsion spring attached to the depth side, shown in FIG. 5B, is one wound clockwise. The torsion springs 103 are deviated in end positions by the length of the coil-shaped middle portions thereof, so that, if the torsion springs were attached to the casings 100L and 100R, a restoring force in a torsional direction would be exerted, causing deviation of the casings 100L and 100R. Thus, in this embodiment, the winding directions of the torsion springs 103 provided are opposite to each other, whereby the force that would cause deviation of the casings 100L and 100R is canceled, thereby stabilizing the casings 100L and 100R in position.

Figure 6:
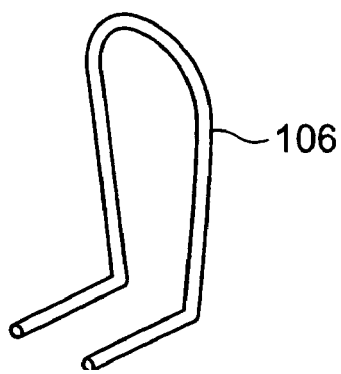
FIG. 6 is a schematic perspective view showing an example of a member constituting the slit forming means of the slit lamp microscope according to the embodiment of the present invention.

Further, as shown in FIGS. 3 and 4, U-shaped springs 106 as shown in FIG. 6 are provided on the inner peripheral surfaces of the casings 100L and 100R. Each U-shaped spring 106 is secured in position, with its end portions being inserted into mounting holes (not shown) formed in the inner peripheral surfaces of the casing 100L, 100R. Each U-shaped spring 106 is mounted to the casing 100L and 100R, with its ends being spaced further apart from each other than in the natural state. That is, each U-shaped spring 106 is mounted such that a restoring force urging its ends toward each other is exerted.

Further, the ends of each U-shaped spring 106 are mounted to positions on the side opposite to the slit blades 107L and 107R with respect to the central axis of the shaft member 102, or to the casings 100L and 100R in the width direction of the slit 54 with respect to the central axis. More specifically, the ends of each U-shaped spring 106 are fixed to positions on the casings 100L and 100R which are higher than the shaft center of the shaft member 102 (e.g., by approximately 1 mm), or to positions by the side of the shaft center. Here, the term shaft center refers to the rotation axis of the shaft member 102.

Due to the above mounting positions, the U-shaped springs 106 urge the casings 100L and 100R so as to press them against the shaft members 102, and at the same time, urge the casings 100L and 100R in a direction opposite to that of the torsion springs 103, i.e., so as to move slit blades 107L and 107R away from each other. In this regard, the U-shaped springs 106 are set such that the force causing the slit blades 107L and 107R to move away from each other is smaller than the urging force of the torsion springs 103 bringing them close to each other. Thus, the resultant force obtained from the urging force of the torsion springs 103 and the urging force of the U-shaped springs 106 acts on the slit blades 107L and 107R so as to bring them close to each other.

On the other hand, with the latter mounting position, the U-shaped springs 106 act so as to press the casings 100L and 100R against the shaft members 102.

Although not shown, the U-shaped springs 106 are mounted on both the front and depth sides as seen in FIGS. 3 and 4 (In the drawings, only the U-shaped spring 106 on the depth side is shown).

The U-shaped springs 106, constructed and arranged as described above, constitute a second urging means of the present invention, which urges the casings 100L and 100R so as to press them against the shaft members 102. Further, by adopting the former mounting position, they also serve as an urging force opposite to the first urging force of the present invention. Here, the reason for using the U-shaped springs 106 as the second urging means is that, by linearly applying the urging force so as to bring the casings 100L and 100R close to each other, it is possible to effectively maintain the protrusions 100L' and 100R' and the shaft members 102 in the contact state.

Further, as shown in FIGS. 2 through 4, on the outer peripheral surfaces of the casings 100L and 100R, bearings 101L and 101R, holding the inter-casing distance varying member 87 therebetween, are arranged so as to be rotatable around protruding shafts and spaced apart from each other by a predetermined distance. The inter-casing distance varying member 87 is vertically movable, and has tapered side surfaces. The bearings 101L and 101R are arranged so as to been gaged with the tapered side surfaces of the inter-casing distance varying member 87. The inter-casing distance varying member 87 and the bearings 101L and 101R constitute engagement portions of the present invention, which are vertically movable and arranged between the casings 100L and 100R to be respectively engaged with them. It should be noted that the inter-casing distance varying member 87 and the bearings 101L and 101R are only provided on the front side in FIGS. 3 and 4.

Figure 7:
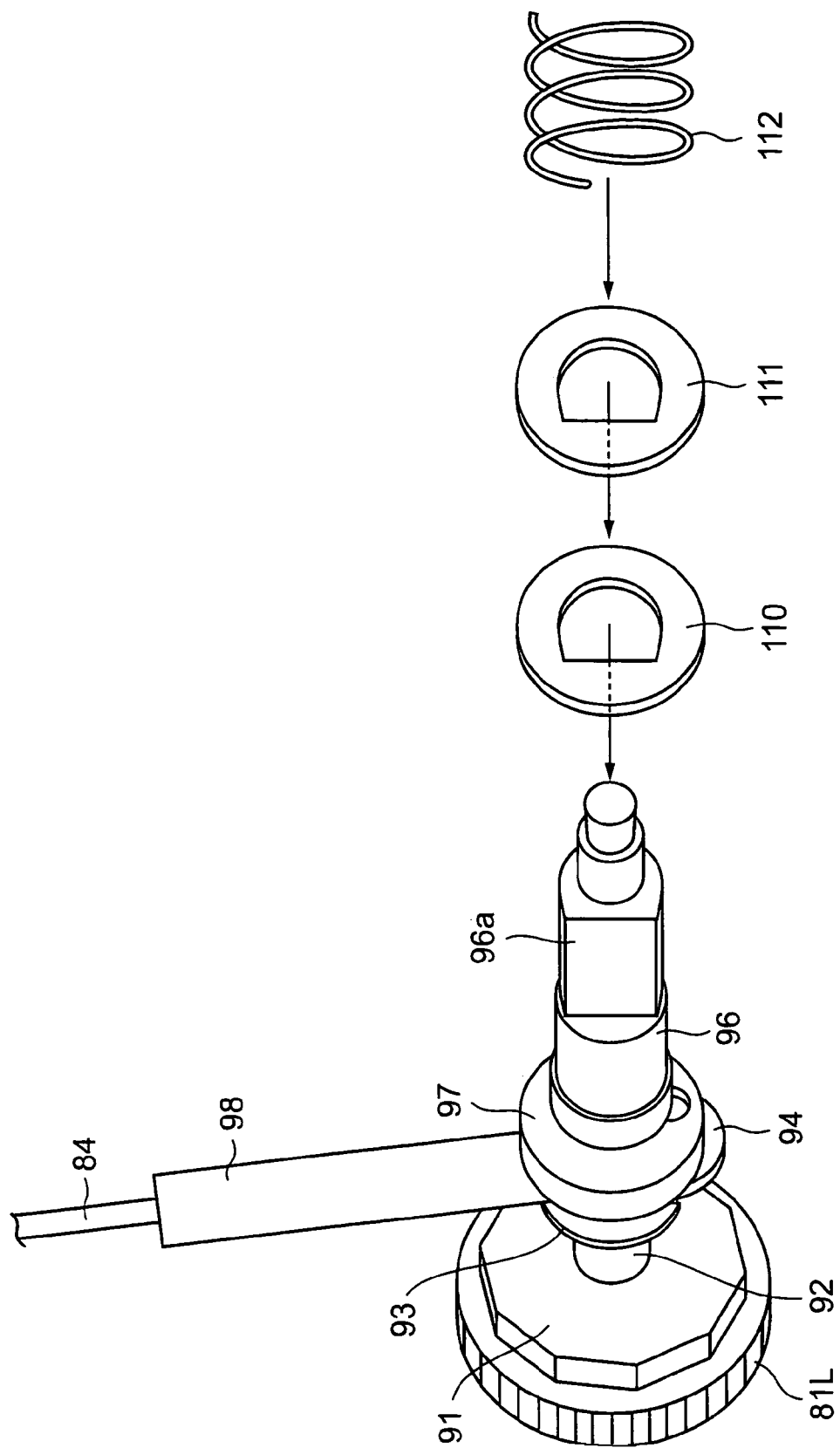
FIG. 7 is a schematic perspective view showing an example of a construction of a brake means of the slit lamp microscope according to an embodiment of the present invention.

Subsequently, referring to FIGS. 2 and 7, the construction of the portion around the operating knobs 81L and 81R will be described. The operating knob 81L is fixed to a fringe 91 provided at one end of a rotation shaft member 92. One end of a shaft portion 94a of a bearing 94 is fixed to an edge portion of a fringe 93 at the other end of the rotation shaft member 92. Similarly, the operating knob 81R is fixed to a fringe 95 provided at one end of a rotation shaft member 96, and the other end of the shaft portion 94a of the bearing 94 is fixed to an edge portion of a fringe 97 at the other end of the rotation shaft member 96.

Further, provided on the ascent/descent shaft 84 inserted into the first post 82 and the second post 83 is a contact member 98 whose lower end is in contact with the bearing 94.

[Slit Width Changing Operation]

The slit width changing operation in the slit lamp microscope of this embodiment, constructed as described above, will be described.

When the operating knob 81L is turned by the examiner, the rotation shaft member 92 is rotated integrally therewith. Thereupon, the bearing 94, fixed to the edge portion of the fringe 93 of the rotation shaft member 92, is rotated so as to draw a circle in a vertical plane (that is, vertically). Then, the contact member 98 whose lower end is in contact with the bearing 94 and the ascent/descent shaft 84, integrated with the contact member 98, are moved vertically in correspondence with the vertical movement of the bearing 94. Then, the ascent/descent table 85 in contact with the upper end of the ascent/descent shaft 84 is moved vertically together with the ascent/descent shaft 84, and the ascent/descent shaft 86 in contact with the upper surface of the ascent/descent table 85 is moved vertically, causing the inter-casing distance varying member 87 to move vertically.

When the inter-casing distance varying member 87 is moved upwards, the bearings 101L and 101R move along the tapered side surfaces of the inter-casing distance varying member 87 so as to gradually increase the distance therebetween. The bearings 101L and the 101R are fixed to the casings 100L and 100R, respectively, and the casings 100L and 100R are constructed so as to be rotatable around the shaft members 102, so that the casings 100L and 100R are rotated around the shaft members 102 so as to enlarge the gap 109. Then, the distance between the slit blades 107L and 107R respectively mounted to the bottom surfaces of the casings 100L and 100R is increased, thereby increasing the width of the slit 54 of the illumination system 8.

In contrast, when the inter-casing distance varying member 87 is moved downwards, the distance between the bearings 101L and 101R decreases, and the casings 100L and 100R are moved around the shaft members 102 so as to diminish the gap 109, thereby reducing the distance between the slit blades 107L and 107R and diminishing the width of the slit 54.

As is apparent from the construction shown in FIG. 2, when the operating knob 81L continues to be turned in the same direction, the bearing 94 repeats the vertical rotation, so that the width of the slit 54 is repeatedly increased and reduced.

Also when the operating knob 81 is operated, the width of the slit 54 is changed in the same manner as in the case of the operating knob 81L.

[Operation and Effects]

The operation and effects of the slit lamp microscope of this embodiment, which thus performs the slit width changing operation, will be described.

When the distance between the casings 100L and 100R (that is, the slit blades 107L and 107R) is changed, the torsion springs 103 and the U-shaped springs 106 mounted to the casings 100L and 100R operate as follows.

First, the torsion springs 103 exert the restoring force so as to bring the slit blades 107L and 107R close to each other.

This causes an increase in the frictional force between the tapered side surfaces of the inter-casing distance changing member 87 and the bearings 101L and 101R, thereby preventing slippage.

In contrast, the U-shaped springs 106 are expanded from the state in which the restoring force is null before being fixed to the casings 100L and 100R, so that they exert the restoring force so as to bring the casings 100L and 100R close to each other. The end portions of the U-shaped strings 106 are fixed at positions substantially beside the shaft members 102, so that the restoring force thereof is exerted so as to press the casings 100L and 100R against the shaft members 102. Thus, even in a case in which the shaft members 102, the protrusions 100L' and 100R' of the casings 100L and 100R, and the ring members 105 do not maintain a proper connection state due to the influence of the heat in the apparatus, errors at the time of production, etc., the casings 100L and 100R can rotate around the shaft members 102 in a stable manner. As a result, the slit 54 formed by the gap between the slit blades 107L and 107R is improved in terms of parallelism, making it possible to generate high precision slit light.

Further, by fixing the ends of the U-shaped springs 106 at positions on the sides opposite to the slit blades 107L and 107R with respect to the shaft member 102 (that is, by arranging the slit blades 107L and 107R below and the U-shaped springs 106 above the shaft members 102), the restoring force of the U-shaped springs 106 is exerted so as to cause the slit blades 107L and 107R to move away from each other. That is, the restoring force of the U-shaped springs 106 and the restoring force of the torsion springs 103 are exerted in opposite directions. As stated above, the restoring force of the U-shaped springs 106 is set smaller than the restoring force of the torsion springs 103, so that the resultant force of these restoring forces is exerted so as to bring the slit blades 107L and 107R close to each other in a less magnitude than when the torsion springs 103 act alone.

Incidentally, as can be seen from the above-described mode of operation, the requisite force for turning the operating knobs 81L and 81R when enlarging the width of the slit 54 greatly depends on the force with which the bearings 101L and 101R push down the inter-casing distance changing member 87, as well as on the respective weights of the bearing 94, the ascent/descent shaft 84, the ascent/descent table 85, the ascent/descent shaft 86, and the inter-casing distance changing member 87. Further, the force with which the bearings 101L and 101R push down the inter-casing distance changing member 87 is obviously defined as the vertical component of the force with which the bearings 101L and 101R hold the tapered side surfaces of the inter-casing distance changing member 87 between themselves. Further, the force with which the bearings 101L and 101R hold the tapered side surfaces of the inter-casing distance changing member 87 between themselves is the same as the force exerted so as to bring the slit blades 107L and 107R close to each other.

Thus, in the slit lamp microscope of this embodiment, the force exerted by the U-shaped springs 106 so as to bring the slit blades 107L and 107R close to each other is smaller, so that the requisite force for turning the operating knobs 81L and 81R is relatively small, thereby facilitating the operation of adjusting the slit width.

Further, when, in particular, the bearings 101L and 101R are in contact with the foot portions of the tapered side surfaces of the Mount-Fuji-shaped inter-casing distance changing member 87, that is, the lower portions of the side surfaces, the force with which the inter-casing distance changing member 87 is pushed down is large, so that it can happen that the inter-casing distance changing member 87 falls to cause the slit 54 to close of itself. In the slit lamp microscope of this embodiment, however, the force with which the pushing-down is effected is reduced, and the urging force to bring the slit blades 107L and 107R close to each other and the urging force to cause them to move away from each other are exerted in a stable manner, whereby it is possible to prevent spontaneous closing of the slit 54.

In brief, the slit lamp microscope of this embodiment, described above, provides the following operational effects: the first urging means for urging the slit blades 107L and 107R so as to bring them close to each other and the second urging means for urging the protrusions 100L' and 100R' of the casings 100L and 100R so as to press them against the shaft members 102 are provided separately, whereby the operation of rotating the casings 100L and 100R, that is, the operation of changing the slit width, can be effected in a satisfactory manner. Further, due to the cancellation of a part of the urging force of the first urging means by the change of the mounting position of the second urging means, the operation of the operating knobs 81L and 81R for changing the slit width is facilitated. Thus, as compared with the conventional construction in which these two actions are managed by a single means, it is possible to provide a more satisfactory slit lamp microscope.

[Regarding the Brake Means for Preventing Spontaneous Closing of the Slit]

To solve the above-mentioned problem of spontaneous closing of the slit 54, ordinary slit lamp microscopes are often equipped with a brake means for braking the rotation of the operating knobs 81L and 81R. As stated above, the conventional brake means uses a felt member and a wave washer. The felt member, however, suffers wear with passage of time of use, making it impossible for the operating knobs 81L and 81R to be braked in a proper manner. Further, use of a wave washer involves a problem in that the contact area in the compressing direction is rather small, so that slippage is likely to occur, allowing the operating knobs 81L and 81R to turn too easily.

The slit lamp microscope of this embodiment is equipped with a brake means capable of preventing such problems. In the following, an example of the construction of the brake means will be described with reference to FIG. 7.

The brake means of this embodiment includes the rotation shaft member 96 on which a D-shaped protrusion 96a with a D-shaped section is formed, a resin washer 110 with a D-shaped opening and a smooth surface, a metal washer 111 with a D-shaped opening, and a spring member 112 for pressurizing the washer 110 and the washer 111 against the rotation shaft member 96. The washers 110 and 111 are fixed to the rotation shaft member 96 by fitting their D-shaped openings onto the D-shaped protrusion 96a.

The washers 110 and 111 and the spring member 112 are accommodated in the operating knob 81R, which is fixed to the rotation shaft member 96 by means of a screw or the like.

The resin washer 110 thus provided is not worn like felt, and, unlike a wave washer, it provides a large contact area. Further, due to the construction in which the washer 110 is fixed to the rotation shaft member 96 by fitting the washer 110 onto the D-shaped protrusion 96a, the washers 110 and 111 are rotated integrally with the operating knobs 81L and 81R, so that a satisfactory braking action is-exerted. Thus, due to this construction, it is possible to provide a brake means superior in durability and providing a satisfactory braking performance.

[Modifications]

Various modifications of the slit lamp microscope of the embodiment of the present invention, described in detail above, will be described.

While in the above embodiment the U-shaped springs 106 serve both as the second urging means for urging the pair of holding members (casings 100L and 100R) against the shaft member 102 and as the second urging means for urging the pair of holding members so as to cause the pair of slit forming members (slit blades 107L and 107R) to move away from each other to thereby achieve space saving and simplification in structure of the apparatus, it is also possible to form the second urging means as separate components. For example, it is also possible to adopt a construction in which, as the second urging means, the U-shaped springs 106 are fixed at positions beside the shaft members 102 or in which, as the second urging means, the torsion springs are mounted at position above the shaft members 102.

Further, while, as described above, it is desirable for the first urging means of the present invention to be torsion springs, it is also possible, as needed, to use some other spring members, such as U-shaped springs. Further, the first urging means is not restricted to spring members; it is also possible to realize a construction capable of exerting a desired urging force by using, for example, rubber members.

Further, while, as described above, it is desirable for the second urging means of the present invention to be U-shaped springs, it is also possible, as needed, to use some other spring members, such as torsion springs. Further, the second urging means is not restricted to spring members; it is also possible to realize a construction capable of exerting a desired urging force by using, for example, rubber members.

The construction described in detail above is only given as an example of the construction for realizing the slit lamp microscope of the present invention. Thus, various modifications are possible as appropriate without departing from the gist of the present invention.

What is claimed is:

1. A slit lamp microscope comprising:
    an illumination system which has a light source emitting illumination light and a pair of slit forming members spaced apart from each other to allow passage of a part of the illumination light and which is adapted to apply slit light to an eye to be examined;
    a slit width changing means having a pair of holding members respectively holding the pair of slit forming members, a shaft member supporting the pair of holding members such that the pair of holding members can rotate in opposite directions, and an engagement portion arranged between the pair of holding members and engaged with each of the pair of holding members, the engagement portion being capable of vertical displacement, the vertical displacement being converted to displacement in the opposite directions of the pair of holding members around the shaft member, the slit width changing means being adapted to change an opening width of the slit in correspondence with the displacement in the opposite directions of the pair of holding members;
    an observation system receiving reflection light of the slit light applied to the eye to be examined;
    a first urging means for urging the pair of holding means such that bring the pair of slit forming members are brought close to each other; and
    a second urging means for urging the pair of holding members such that the pair of holding members are pressed against the shaft member,
    wherein the urging force of the second urging means is weaker than that of the first urging means.

2. A slit lamp microscope to claim 1, wherein the second urging means is a spring member.

3. A slit lamp microscope according to claim 2, wherein the spring member is a U-shaped spring whose ends are respectively fixed to the pair of holding members.

4. A slit lamp microscope according to claim 3, wherein the pair of slit forming members are held at bottom surfaces of the pair of holding members,
    wherein the shaft member supports the pair of holding members at a position above the pair of slit forming members, and
    wherein the ends of the U-shaped spring as the second urging means are each fixed to the pair of holding members on either side of the shaft member and at one of a position opposite to the slit forming members divided by a linear line passing through an axial center of the shaft member or a position on the linear line.

* * * * *